United States Patent [19]

Iwao et al.

[11] Patent Number: 5,942,249
[45] Date of Patent: Aug. 24, 1999

[54] COMPOSITION FOR ORAL ADMINISTRATION CONTAINING PYRIDAZINONE COMPOUNDS

[75] Inventors: Toru Iwao; Tomoyo Seki; Nobuo Kondo; Yasuo Ueda, all of Hirakata, Japan

[73] Assignees: The Green Cross Corporation, Osaka; Nissan Chemical Industries, Ltd., Tokyo, both of Japan

[21] Appl. No.: 09/014,563

[22] Filed: Jan. 28, 1998

[30] Foreign Application Priority Data

Jan. 31, 1997 [JP] Japan .................... 9-019115

[51] Int. Cl.⁶ ........................ A61K 31/53; A61K 9/20
[52] U.S. Cl. ................ 424/465; 424/464; 514/236.5; 514/960; 514/970
[58] Field of Search ................ 514/310, 236.5, 514/960, 970; 424/464, 465

[56] References Cited

U.S. PATENT DOCUMENTS

| | | | |
|---|---|---|---|
| 5,137,730 | 8/1992 | Dennis et al. ............ | 424/465 |
| 5,167,947 | 12/1992 | Geary ..................... | 424/1.77 |
| 5,202,323 | 4/1993 | Tanikawa et al. ......... | 514/236.5 |
| 5,314,883 | 5/1994 | Tanikawa et al. ......... | 514/236.5 |
| 5,318,968 | 6/1994 | Tanikawa et al. ......... | 514/236.5 |
| 5,364,646 | 11/1994 | Gruber et al. ............ | 424/464 |
| 5,424,075 | 6/1995 | Daher et al. ............. | 424/465 |

FOREIGN PATENT DOCUMENTS

95/22329   8/1995   WIPO .

*Primary Examiner*—Robert H. Harrison
*Attorney, Agent, or Firm*—Sughrue, Mion, Zinn, Macpeak & Seas, PLLC

[57] ABSTRACT

A composition for oral administration which contains a pyridazinone compound of the formula (I)

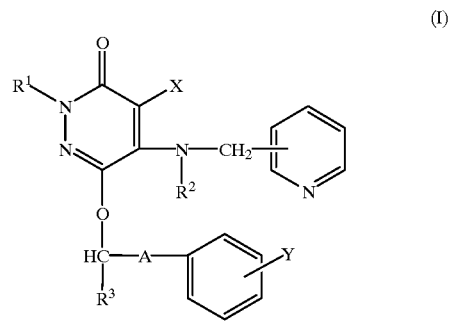

wherein $R^1$, $R^2$ and $R^3$ are each independently a hydrogen atom or a lower alkyl, X is a halogen atom, a cyano or a hydrogen atom, Y is a halogen atom, a trifluoromethyl or a hydrogen atom, and A is a $C_1$–$C_8$ alkylene optionally substituted by hydroxy, or a pharmacologically acceptable salt thereof, and an organic acid. According to the present invention, a composition for oral administration which is stable to heat, light, moisture and the like and which shows improved dissolution and absorption of a pyridazinone compound can be provided.

9 Claims, 2 Drawing Sheets

F I G. 2
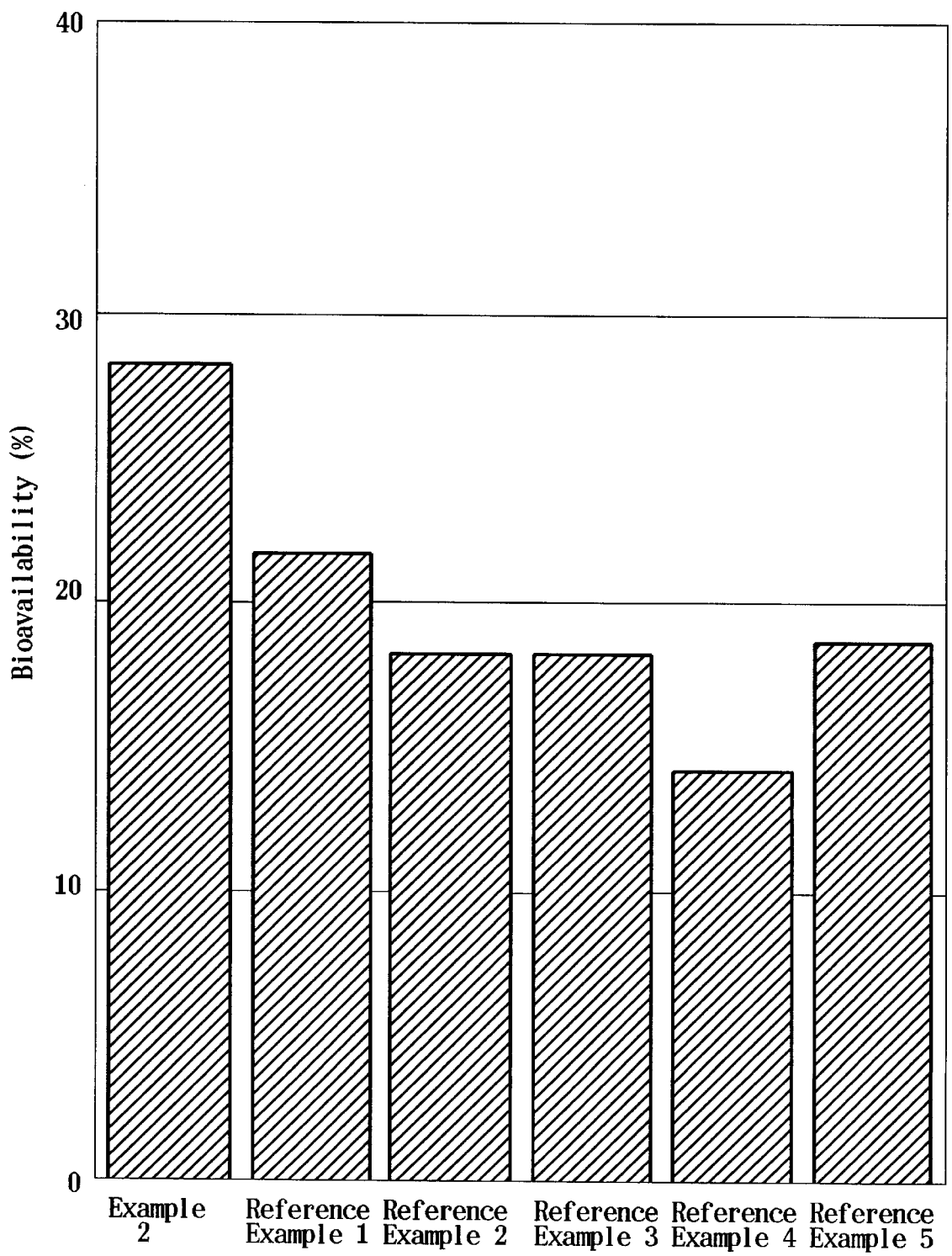

COMPOSITION FOR ORAL ADMINISTRATION CONTAINING PYRIDAZINONE COMPOUNDS

TECHNICAL OF THE INVENTION

The present invention relates to a composition for oral administration, which contains a pyridazinone compound of the formula (I):

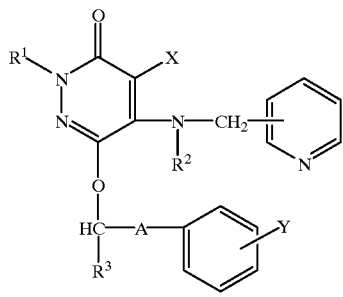

wherein $R^1$, $R^2$ and $R^3$ are each independently a hydrogen atom or a lower alkyl, X is a halogen atom, a cyano or a hydrogen atom, Y is a halogen atom, a trifluoromethyl or a hydrogen atom, and A is a $C_1$–$C_8$ alkylene which may be substituted by hydroxy, or a pharmacologically acceptable salt thereof (hereinafter to be referred to as pyridazinone compounds).

BACKGROUND OF THE INVENTION

The pyridazinone compounds to be used in the present invention are known in literatures, are known to have superior platelet aggregation inhibitory activity, heart stimulating activity, vasodilative activity, anti SRS-A (Slow Reacting Substances of Anaphylaxis) activity, thromboxane $A_2$ synthase inhibitory activity and the like, and are expected to be useful as antiplatelet agents and the like (EP 482208, EP 744950).

The present inventors have now found with regard to compositions for oral administration, which contains pyridazinone compounds, that (a) pyridazinone compounds are relatively stable to heat, light, moisture and the like but show less dissolution after oral administration because their solubility in water starts falling at about pH 4 and they become hardly soluble at the neutral range, and (b) bioavailability (hereinafter to be abbreviated as BA) which shows absorption by dogs after fasting is low (about 10%) and the absorption shows great interindividual differences. They have concluded, therefore, that these problems in terms of dissolution and absorption of pyridazinone compounds need to be resolved before using the compounds for preparations for oral administration.

SUMMARY OF THE INVENTION

It is therefore an object of the present invention to provide a composition for oral administration, which shows improved dissolution and absorption of pyridazinone compounds.

According to the present invention, the dissolution and absorption of pyridazinone compounds can be improved by adding an organic acid to a composition thereof, rather than by a typical formulation method which cannot provide sufficient effects, which finding has led to the completion of the present invention.

Accordingly, the present invention provides a composition for oral administration which contains a pyridazinone compound of the formula (I)

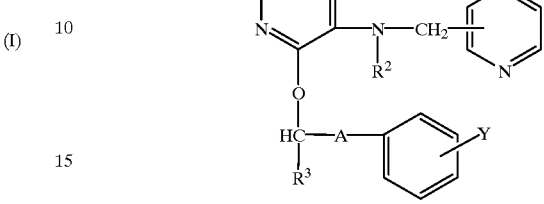

wherein
$R^1$, $R^2$ and $R^3$ are each independently a hydrogen atom or a lower alkyl;
X is a halogen atom, a cyano or a hydrogen atom;
Y is a halogen atom, a trifluoromethyl or a hydrogen atom; and
A is a $C_1$–$C_8$ alkylene optionally substituted by hydroxy, or a pharmacologically acceptable salt thereof, and an organic acid.

BRIEF DESCRIPTION OF THE DRAWINGS

FIG. 2 is a graph showing BA of beagle dogs tested in Experimental Example 2.

DETAILED DESCRIPTION OF THE INVENTION

Figure 1:
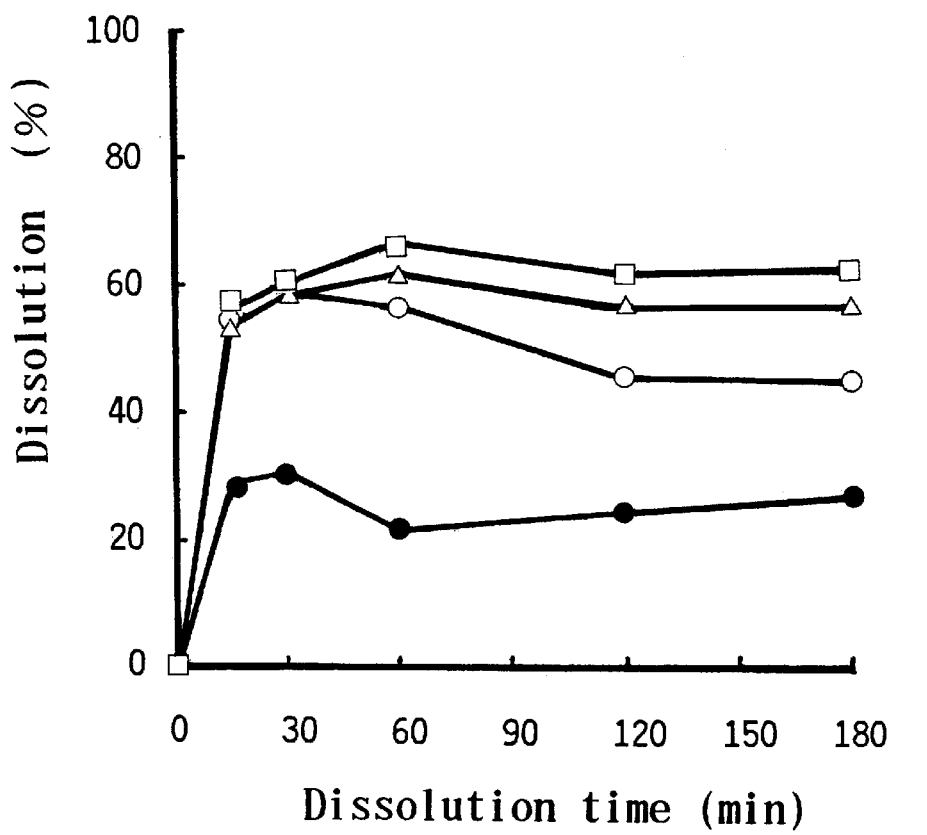
FIG. 1 is a graph showing the results of the dissolution test of Experimental Example 1.

The symbols used in the present specification are explained in the following. The lower alkyl at $R^1$, $R^2$ and $R^3$ may be linear or branched and has 1 to 6 carbon atoms. Examples thereof include methyl, ethyl, n-propyl, isopropyl, n-butyl, isobutyl, sec-butyl, t-butyl, pentyl, hexyl and the like. Preferred $R^1$ and $R^2$ are hydrogen atoms and preferred $R^3$ is a hydrogen atom or an alkyl having 1 to 4 carbon atoms.

The alkyl having 1 to 4 carbon atoms at $R^3$ is exemplified by methyl, ethyl, n-propyl, isopropyl, n-butyl, isobutyl, sec-butyl, t-butyl and the like.

The halogen atom at X and Y is fluorine atom, chlorine atom, bromine atom or iodine atom. Preferred X is halogen atom and preferred Y is halogen atom or hydrogen atom.

The alkylene having 1 to 8 carbon atoms at A which may be substituted by hydroxy may be linear or branched. Examples thereof include methylene, ethylene, propylene, butylene, pentylene, hexylene, heptylene, octylene, 2,2-dimethylethylene, 2,2-diethylethylene, 2,2-di-n-propylethylene, hydroxymethylene, 1-hydroxyethylene, 2-hydroxyethylene, 3-hydroxypropylene and the like. Preferred A is an alkylene having 1 to 5 carbon atoms which is optionally substituted by hydroxy.

While the position of the bond of methylene group and pyridine ring in formula (I) is not particularly limited, it is preferably 3-position relative to nitrogen atom of the pyridine ring. Y may be bonded at any position on the benzene ring, but preferably at 4-position.

In the formula (I), a pyridazinone compound (I) wherein $R^1$ is a hydrogen atom is preferable.

In particular, a pyridazinone compound of the formula (I) wherein $R^1$ and $R^2$ are hydrogen atoms, $R^3$ is a hydrogen atom or an alkyl having 1 to 4 carbon atoms, X is a halogen atom, Y is a halogen atom or a hydrogen atom, and A is an alkylene having 1 to 5 carbon atoms which may be substituted by hydroxy is preferable.

More preferable pyridazinone compound (I) includes 4-bromo-6-(3-phenylpropoxy)-5-(3-pyridylmethylamino)-3(2H)-pyridazinone, 4-chloro-6-(3-phenylpropoxy)-5-(3-pyridylmethylamino)-3(2H)-pyridazinone, 4-chloro-6-[3-(4-chlorophenyl)propoxy]-5-(3-pyridylmethylamino)-3(2H)-pyridazinone, 4-bromo-6-[3-(4-chlorophenyl)propoxy]-5-(3-pyridylmethylamino)-3(2H)-pyridazinone, 4-bromo-6-(2,2-dimethyl-3-phenylpropoxy)-5-(3-pyridylmethylamino)-3(2H)-pyridazinone, 4-chloro-6-(2,2-dimethyl-3-phenylpropoxy)-5-(3-pyridylmethylamino)-3(2H)-pyridazinone, 4-bromo-6-[3-(4-chlorophenyl)-2,2-dimethylpropoxy]-5-(3-pyridylmethylamino)-3(2H)-pyridazinone, 4-chloro-6-[3-(4-chlorophenyl)-2,2-dimethylpropoxy]-5-(3-pyridylmethylamino)-3(2H)-pyridazinone, 4-bromo-6-[3-(4-chlorophenyl)-3-hydroxypropoxy]-5-(3-pyridylmethylamino)-3(2H)-pyridazinone, 4-chloro-6-[3-(4-chlorophenyl)-3-hydroxypropoxy]-5-(3-pyridylmethylamino)-3(2H)-pyridazinone, 4-bromo-6-[3-(4-chlorophenyl)-2-hydroxypropoxy]-5-(3-pyridylmethylamino)-3(2H)-pyridazinone and 4-chloro-6-[3-(4-chlorophenyl)-2-hydroxypropoxy]-5-(3-pyridylmethylamino)-3(2H)-pyridazinone.

The pyridazinone compound (I) of the present invention encompasses stereoisomers and optical isomers.

The pyridazinone compound (I) can be produced by, for example, the method disclosed in EP 482208, or other method.

The pharmacologically acceptable salt of pyridazinone compound (I) may be a salt with an inorganic acid (e.g., hydrochloride, hydrobromide, phosphate, sulfate and the like), a salt with an organic acid (e.g., acetate, succinate, maleate, fumarate, malate, tartrate and the like), and the like. The pyridazinone compound (I) can be converted to the above-mentioned salts by a known method.

The organic acid to be used in the present invention includes, for example, citric acid, succinic acid, maleic acid, fumaric acid, malic acid, tartaric acid and the like, with particular preference given to citric acid. The organic acid is preferably added in a proportion of 0.05–20 parts by weight per part by weight of the pyridazinone compound.

When to add an organic acid is not particularly limited and an organic acid may be added before granulation or after granulation but before compression. Considering the absorption of the pyridazinone compound, an organic acid is preferably added before granulation.

By adding an organic acid to a pyridazinone compound, the dissolution and absorption of the pyridazinone compound can be improved, and a composition for oral administration which is stable to heat, light, moisture and the like can be provided.

When formulating the composition for oral administration of the present invention, the pyridazinone compound is preferably micronized. The pyridazinone compound as a bulk powder has an average particle size of about 20 μm. Micronization by a known method can make the average particle size about 7–10 μm. The micronization of the pyridazinone compound contributes to improvement in dissolution and absorption.

The composition for oral administration of the present invention can be formulated into a dosage form of tablet, capsule, powder, granule, pill and the like by a conventional method using excipients, binders, disintegrators, lubricants and the like. The excipients and the like to be used are not particularly limited. Examples of excipient include lactose, corn starch, sucrose, glucose, mannitol, sorbit, crystalline cellulose, silicon dioxide and the like. Examples of binder include polyvinyl alcohol, polyvinyl ether, ethylcellulose, methylcellulose, gum arabic, tragacanth, gelatin, shellac, hydroxypropylcellulose, hydroxypropylmethylcellulose, hydroxypropyl starch, polyvinylpyrrolidone and the like. Examples of disintegrator include starch, agar, gelatin powder, crystalline cellulose, calcium carbonate, sodium hydrogencarbonate, calcium citrate, dextrin, pectin, carboxymethylcellulose calcium, low substitution hydroxypropylcellulose, croscarmellose sodium, partly pregelatinized starch and the like. Examples of lubricant include magnesium stearate, talc, polyethylene glycol, silica, hydrogenated vegetable oil and the like. The use of lactose as an excipient or the use of hydroxypropylcellulose as a binder may unexpectedly lead to undesirable coloring of the preparation. Thus, the use of other excipients and other binders is preferable. Preferable excipient may be crystalline cellulose, corn starch, mannitol and the like. Preferable binder may be hydroxypropylmethylcellulose and the like.

The excipient, binder, disintegrator and lubricant are contained in a proportion of preferably 10–150 parts by weight, 0.5–10 parts by weight, 1–20 parts by weight and 0.1–1.5 parts by weight, respectively, per part by weight of the pyridazinone compound.

While the dosage form of the inventive pharmaceutical composition is not limited, it is preferably tablet. When tablets are prepared, for example, water is added to an admixture of ingredients in a proportion of about 5–35% (w/w), and the resulting mixture is granulated by a stirring-granulation method using a high speed mixer and the like, followed by compression (wet granulation compression method), or the respective ingredients are mixed homogeneously, followed by compression molding (direct compression method), or they are prepared by other method. To the tablets is preferably applied a coating base material such as a commercially available HA "SANKYO" manufactured by Sankyo Co., Ltd. and the like to increase resistance to moisture.

The present invention is explained in detail by way of Examples and Experimental Examples, to which the present invention is not limited.

In the following Examples and Experimental Examples, 4-bromo-6-[3-(4-chlorophenyl)propoxy]-5-(3-pyridylmethylamino)-3(2H)-pyridazinone hydrochloride (hereinafter to be simply referred to as pyridazinone hydrochloride) prepared by a conventional method was used as a pyridazinone compound.

EXAMPLE 1

Tablets were prepared, which contained pyridazinone hydrochloride (10.0 mg) as an active ingredient, citric acid (5.0 mg, manufactured by Showa Chemical Industry Co., Ltd.) as an organic acid, lactose (123.0 mg) as an excipient, hydroxypropylcellulose (4.0 mg, HPC-SL, manufactured by Nippon Soda Co., Ltd.) as a binder, croscarmellose sodium (7.0 mg, Ac-Di-Sol, manufactured by Asahi Chemical Industry Co., Ltd.) as a disintegrator and magnesium stearate (1.0 mg, manufactured by TAIHEI CHEMICAL Co., Ltd.) as a lubricant.

The tablets were made by the wet granulation compression method, wherein the active ingredient, organic acid, excipient, binder and disintegrator were mixed, to which about 12% (w/w) of water was added, and the mixture was granulated by a stirring-granulation method. Then, the obtained granules were dried at 80° C. for about 30 min, and passed through a 32 mesh sieve to give a powder for compression. The lubricant and disintegrator were added to the obtained powder, and the mixture was compressed with a die and a punch having 7.5 mm φ and typical R surfaces to give tablets.

The active ingredient, pyridazinone hydrochloride, was prepared by dry-micronization of a bulk powder with a turbo mill micronizer (TJ-60, manufactured by Turbo Kogyo Co., LTD., air pressure 7.5–8.5 kg/cm$^2$, feed control 8.0–8.5). The average particle size of the bulk powder was about 20 μm. The obtained micronization product had an average particle size of about 7 μm. The average particle size was an average of three determinations performed using a particle size measuring device (CIS-1, manufactured by GALAI), hereinafter the same.

EXAMPLE 2

In the same manner as in Example 1 except that the amount of citric acid was changed to 15.0 mg and the amount of lactose was changed to 113.0 mg, tablets were prepared.

EXAMPLE 3

In the same manner as in Example 1 except that the amount of citric acid was changed to 50.0 mg and the amount of lactose was changed to 78.0 mg, tablets were prepared.

EXAMPLE 4

In the same manner as in Example 1 except that the amount of citric acid was changed to 7.5 mg and the amount of lactose was changed to 120.5 mg, tablets were prepared.

EXAMPLE 5

In the same manner as in Example 1, tablets were prepared, which contained pyridazinone hydrochloride (10.0 mg) as an active ingredient, citric acid as an organic acid (15.0 mg, manufactured by Showa Chemical Industry Co., Ltd.), crystalline cellulose (15.0 mg, Avicel PH101, manufactured by Asahi Chemical Industry Co., Ltd.) as an excipient, hydroxypropylmethylcellulose (4.0 mg, TC-5R, manufactured by Shin-Etsu Chemical Co., Ltd.) as a binder, low substitution hydroxypropylcellulose (7.0 mg, L-HPC, manufactured by Shin-Etsu Chemical Co., Ltd.) as a disintegrator, and magnesium stearate (1.0 mg) as a lubricant.

The active ingredient, pyridazinone hydrochloride, was prepared by micronization of a bulk powder with a pin mill micronizer (KOLLOPLEX 160Z, manufactured by Powrex Corporation, pin rotation 9000 rpm, supply slit width ca. 1 cm, charge amount 500 g). The pin mill micronization product had an average particle size of about 10 μm.

EXAMPLE 6

In the same manner as in Example 5 except that low substitution hydroxypropylcellulose was not added, the amount of crystalline cellulose was changed to 90.0 mg and partly pregelatinized starch (30.0 mg, PCS, manufactured by Asahi Chemical Industry Co., Ltd.) was added as a disintegrator, tablets were obtained.

EXAMPLE 7

In the same manner as in Example 5 except that the amount of crystalline cellulose was changed to 56.5 mg, corn starch (56.5 mg, manufactured by MATSUTANI KAGAKU KOGYO Co., Ltd.) was added as an excipient and citric acid was added after passing through a sieve, tablets were obtained.

EXAMPLE 8

In the same manner as in Example 6 except that the amount of crystalline cellulose was changed to 45.0 mg and corn starch was added in an amount of 45.0 mg, tablets were obtained.

EXAMPLE 9

In the same manner as in Example 8 except that corn starch was changed to D-mannitol (manufactured by TOWA CHEMICAL INDUSTRY Co., Ltd.), tablets were obtained.

EXAMPLE 10

Tablets were prepared, which contained pyridazinone hydrochloride (10.0 mg) as an active ingredient, citric acid (15.0 mg) as an organic acid, crystalline cellulose (75.0 mg) as an excipient, lactose (15.0 mg), hydroxypropylmethylcellulose (4.0 mg) as a binder, partly pregelatinized starch (30.0 mg) as a disintegrator and magnesium stearate (1.0 mg) as a lubricant.

The tablets were prepared by the direct compression method. To be specific, the active ingredient and the organic acid were mixed, and the obtained mixture was micronized with a pin mill as in Example 5, to which an excipient, a binder and a disintegrator, respectively passed through a sieve, were added. Then, a lubricant was added thereto to give a powder for compression. Using a die and a punch having 7.5 mm φ and typical R surfaces, tablets were produced.

EXAMPLES 11–13

According to the wet granulation compression method of Example 1, naked tablets having the formulations shown in Table 1 were prepared, which tablets were coated with a coating agent [coating base HA "SANKYO" (manufactured by Sankyo Co., Ltd.) and triacetine] by a pan coating method to give film-coated tablets.

TABLE 1

| Example | 11 | 12 | 13 |
|---|---|---|---|
| ingredients (naked tablet) | 8 mg tablet | 2 mg tablet | 0.5 mg tablet |
| pin mill micronized product of pyridazinone hydrochloride | 8.0 | 2.0 | 0.5 |
| citric acid | 15.0 | 9.0 | 9.0 |
| crystalline cellulose | 106.5 | 66.7 | 68.2 |
| hydroxypropylmethylcellulose | 4.5 | 2.7 | 2.7 |
| low substitution hydroxypropylcellulose | 15.0 | 9.0 | 9.0 |
| magnesium stearate | 1.0 | 0.6 | 0.6 |
| subtotal (mg) | 150.0 | 90.0 | 90.0 |
| tablet diameter (mm φ) | 7.5 | 6.5 | 6.5 |
| (coating film) | | | |
| HA "SANKYO" | 13.7 | 8.2 | 8.2 |
| triacetine | 1.3 | 0.8 | 0.8 |
| total (mg) | 165.0 | 99.0 | 99.0 |

REFERENCE EXAMPLE 1

In the same manner as in Example 1 except that citric acid was not added and the amount of lactose was changed to 128.0 mg, tablets were obtained.

REFERENCE EXAMPLE 2

In the same manner as in Example 1 except that citric acid was not added, the amount of lactose was changed to 127.0 mg, and sugar ester (1.0 mg, DK ester SS, manufactured by DAI-ICHI KOGYO SEIYAKU CO., LTD.) was added as a surfactant, tablets were obtained.

REFERENCE EXAMPLES 3–5

A bulk powder (2 g) of pyridazinone hydrochloride and a water soluble polymer (10 g) were mixed, to which methanol or a methanol/dichloromethane (1/1) mixed solution was added, followed by dissolution under heating at 50° C. The mixture was evaporated to dryness in a rotary evaporator at 50° C. and dried under reduced pressure overnight at 60° C. The dry product was micronized in a sample mill and dried under reduced pressure overnight at 60° C. to give an amorphous composition. Using, as the water soluble polymers, polyvinylpyrrolidone vinylacetate (Kollidon VA64, manufactured by BASF), hydroxypropylmethylcellulose and hydroxypropylmethylcellulose phthalate (HP-55, manufactured by Shin-Etsu Chemical Co., Ltd.), the compositions of Reference Examples 3 to 5 were obtained.

Experimental Example 1: Dissolution Test

The tablets of Examples 1 to 3 and Reference Example 1 were subjected to a dissolution test using a phosphate buffer (pH 6.8). The test followed the dissolution test (puddle method) according to 12th Edition Japan Pharmacopoeia, wherein the number of rotation was 100 rpm, the amount of test solution was 900 ml and the amount of sampling and the amount of supplementary solution were both 10 ml.

The sample was centrifuged at 15000 rpm for 10 min, and an internal standard solution (0.5 ml) was added to 0.5 ml of the supernatant thus obtained. The obtained mixture was subjected to HPLC under the following conditions.
HPLC conditions
Standard solution: Pyridazinone hydrochloride (0.020 g) was accurately weighed and dissolved in methanol to make the total amount precisely 20 ml. One milliliter was taken therefrom and phosphate buffer (pH 6.8) was added to make the total amount precisely 100 ml. To 0.5 ml thereof was added an internal standard solution (0.5 ml) to give a standard solution.
Internal standard solution: 2-Acetonaphtone (5 $\mu$g/ml) was dissolved in a methanol.acetonitrile mixed solution (15:9) to give an internal standard solution.
Detector: UV absorptiometer (measurement wavelength 290 nm)
Column: Nucleosil 100-5-C18 ($\phi$4.6×250 mm, manufactured by GL Science)
Column temperature: 40° C.
Mobile phase: water.methanol.acetonitrile mixture (6:5:3)
Flow rate: 1.4 ml/min
Analysis time: 20 min
Feed amount: 10 $\mu$l The relationship between percent dissolution and dissolution time is shown in FIG. 1. As shown in FIG. 1, the tablets containing citric acid showed faster dissolution pattern than the tablets without citric acid.

Experimental Example 2: Absorption Test

The compositions of Example 2 and Reference Example 1 to 5 were subjected to absorption test using beagle dogs. The test included administration (10 mg/kg body weight) of the compositions to the dogs (body weight 10–12 kg, n=5 or 10) fasted for 20 hr before the administration, fasting the dogs for 5 hr after the administration, and time-course determination of the drug concentration in plasma after the administration. The drug concentration in plasma was determined by HPLC under the following conditions.

HPLC conditions

Detector: UV absorptiometer (measurement wavelength 286 nm)
Column: Superspher RP-18e ($\phi$04.0×250 mm, manufactured by Merck) Guardcolumn: Lichrospher RP-18e ($\phi$4.0×4.0 mm, 5 $\mu$m, manufactured by Merck)
Mobile phase: CH$_3$CN/10 mM CH$_3$COONa=42/58
Flow rate: 1.0 ml/min
Column temperature: 50° C.
Analysis time: 30 min
Feed amount: 30 $\mu$l The maximum drug concentration (Cmax) in plasma after the administration of the composition is shown in Table 2.

TABLE 2

|  | Ex. 2 | Ref. Ex. 1 | Ref. Ex. 2 | Ref. Ex. 3 | Ref. Ex. 4 | Ref. Ex. 5 |
|---|---|---|---|---|---|---|
| Cmax (ng/ml) | 751.4 | 726.5 | 543.9 | 439.2 | 560.6 | 408.1 |

The BA of each composition in beagle dogs is shown in FIG. 2. The tablets of Example 2 showed a BA of about 30%, which indicated about three times greater absorption than the bulk powder of pyridazinone hydrochloride. On the other hand, the best BA of the compositions of Reference Examples was about 20%. The interindividual difference seen in the tablets of Example 2 was not more than one-second of the difference found with the compositions of Reference Examples.

The tablets of Example 2 were subjected to an absorption test after post-feeding administration. The test was done in the same manner as in the above fast-administration except that standard solid feed (ca. 300 g) was given 30 min before administration of the tablets. The results of absorption by post-feeding administration are shown in Table 3 along with the results of fast-administration.

TABLE 3

| Example 2 | Cmax (ng/ml) | BA (%) |
|---|---|---|
| fast-administration | 751.4 | 28.2 |
| post-feeding administration | 1054.8 | 29.0 |

The average BA of post-feeding administration was 29%, which was similar to the result obtained by fast-administration.

According to the present invention, a composition for oral administration which is stable to heat, light, moisture and the like and which shows improved dissolution and absorption of a pyridazinone compound can be provided.

This application is based on application No. 19115/1997 filed in Japan, the content of which is incorporated hereinto by reference.

What is claimed is:
1. A composition for oral administration which comprises a pyridazinone compound of the formula (I)

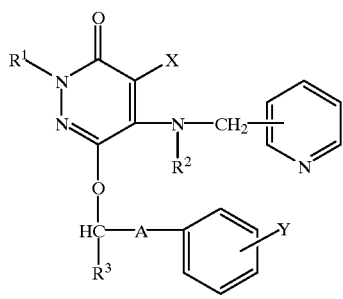 (I)

wherein

R¹, R² and R³ are each independently a hydrogen atom or a lower alkyl;

X is a halogen atom, a cyano or a hydrogen atom;

Y is a halogen atom, a trifluoromethyl or a hydrogen atom; and

A is a $C_1$–$C_8$ alkylene optionally substituted by hydroxy, or a pharmacologically acceptable salt thereof, and an organic acid.

2. The composition for oral administration of claim 1, wherein, in the formula (I), R¹ is a hydrogen atom.

3. The composition for oral administration of claim 1, wherein the pyridazinone compound of the formula (I) is 4-bromo-6-[3-(4-chlorophenyl)propoxy]-5-(3-pyridylmethylamino)-3(2H)-pyridazinone.

4. The composition for oral administration of any one of claims 1 to 3, wherein the organic acid is citric acid.

5. The composition for oral administration of claim 1, wherein the pyridazinone compound or the pharmacologically acceptable salt thereof is micronized.

6. The composition for oral administration of claim 1, comprising at least one excipient selected from the group consisting of crystalline cellulose, corn starch and mannitol.

7. The composition for oral administration of claim 1, further comprising hydroxpropylmethlcellulose as a binder.

8. The composition for oral administration of claim 1, which is a tablet.

9. The composition for oral administration of claim 8, which is coated with a moisture-proof coating.

* * * * *